United States Patent [19]

Oe et al.

[11] 4,386,092
[45] May 31, 1983

[54] HETEROCYCLIC-SUBSTITUTED OXOALKANOIC ACID DERIVATIVES

[75] Inventors: Takanori Oe, Nakatsu; Minoru Moriwaki, Fukuoka; Kazuhiro Goto; Masao Hisadome, both of Nakatsu, all of Japan

[73] Assignee: Yoshitomi Pharmaceutical Industries, Ltd., Osaka, Japan

[21] Appl. No.: 297,696

[22] PCT Filed: Jan. 13, 1981

[86] PCT No.: PCT/JP81/00007
§ 371 Date: Aug. 28, 1981
§ 102(e) Date: Aug. 28, 1981

[87] PCT Pub. No.: WO81/02013
PCT Pub. Date: Jul. 23, 1981

[30] Foreign Application Priority Data

Jan. 16, 1980 [JP] Japan .................................. 55-4012

[51] Int. Cl.$^3$ ................. A61K 31/425; A61K 31/435; C07D 471/04; C07D 513/04
[52] U.S. Cl. ..................................... 424/256; 424/270; 546/112; 546/121; 548/154
[58] Field of Search ................ 546/121, 112; 548/154; 424/256, 270

[56] References Cited

U.S. PATENT DOCUMENTS 4,267,339 5/1981 Tedeschi ............................. 548/154

FOREIGN PATENT DOCUMENTS 1076089 7/1967 United Kingdom ................. 546/121
1493043 11/1977 United Kingdom ................. 548/154

Primary Examiner—Robert T. Bond
Attorney, Agent, or Firm—Berman, Aisenberg & Platt

[57] ABSTRACT

A heterocyclic-substituted oxoalkanoic acid derivative having immunomodulatory activities of the formula:

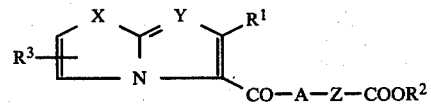

wherein $R^1$ is hydrogen, lower alkyl, phenyl which may be substituted by at least one substituent selected from halogen, lower alkyl, lower alkoxy, mono- or di-lower alkyl amino-substituted lower alkoxy, lower alkylthio, lower alkylsulfinyl, amino, nitro and cyano at any position(s) on the nucleus, thienyl or furyl, each of $R^2$ and $R^3$ is hydrogen or lower alkyl, A is lower alkylene, X is sulfur or vinylene, Y is nitrogen or methine which may be substituted by lower alkyl, Z is carbonyl or direct bond.

10 Claims, No Drawings

HETEROCYCLIC-SUBSTITUTED OXOALKANOIC ACID DERIVATIVES

TECHNICAL FIELD

The present invention relates to a novel and therapeutically valuable heterocyclic-substituted oxoalkanoic acid derivative.

DISCLOSURE OF INVENTION

The heterocyclic-substituted acid derivatives of the present invention are represented by the formula:

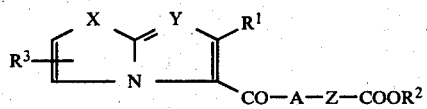
(I)

wherein $R^1$ is hydrogen, lower alkyl, phenyl which may be substituted by at least one substituent selected from halogen, lower alkyl, lower alkoxy, mono- or di-lower alkyl aminosubstituted lower alkoxy, lower alkylthio, lower alkylsulfinyl, amino, nitro and cyano at any position(s) on the nucleus, thienyl or furyl, each of $R^2$ and $R^3$ is hydrogen or lower alkyl, A is lower alkylene, X is sulfur or vinylene, Y is nitrogen or methine which may be substituted by lower alkyl, and Z is carbonyl or direct bond.

In this specification, halogen means chlorine, bromine, fluorine, etc., lower alkyl means the one having 1 to 4 carbon atoms such as methyl, ethyl, propyl, isopropyl or butyl, lower alkoxy means the one having 1 to 4 carbon atoms such as methoxy, ethoxy, propoxy or butoxy, lower alkylene means the one having 1 to 4 carbon atoms such as methylene, ethylene, trimethylene, propylene, ethylidene or propylidene.

The compounds of formula (I) can be prepared by one of the following Methods (1) to (3):

Method (1): The compounds of formula (I) wherein Z is carbonyl, namely the compounds of formula:

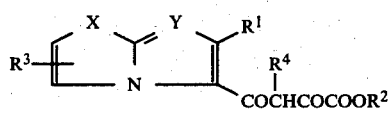
(II)

wherein $R^4$ is hydrogen or lower alkyl and other symbols are as defined above, can be prepared by subjecting a compound of the formula:

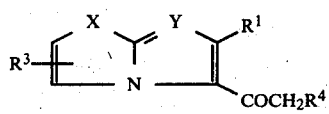
(III)

wherein each symbol is as defined above, to condensation reaction with a compound of the formula:

(IV)

wherein $R^2$ is as defined above.

The reaction is carried out in a suitable solvent (methanol, ethanol, tetrahydrofuran, dioxane, benzene, toluene, etc., or a mixture thereof) in the presence of a basic catalyst (potassium ethoxide, sodium ethoxide, sodium methoxide, sodium hydride, etc.) at 30° to 100° C. for 30 minutes to 3 hours.

Method (2): The compounds of formula (I) wherein Z is direct bond, namely the compounds of the formula:

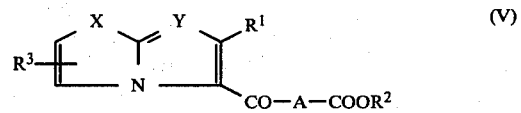
(V)

wherein each symbol is as defined above, can be prepared by subjecting a compound of the formula:

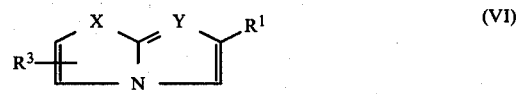
(VI)

wherein each symbol is as defined above, to condensation reaction with a compound of the formula:

HalCO-A-COOR$^2$  (VII)

wherein Hal is chlorine or bromine and other symbols are as defined above.

The reaction is carried out in a suitable solvent (acetone, benzene, toluene, xylene, methylene chloride, chloroform, dichloroethane, dioxane, etc., or a mixture thereof) in the presence of a deacidifying agent (pyridine, triethylamine, sodium carbonate, potassium carbonate, sodium hydrogencarbonate, sodium acetate, etc.) at 30° to 150° C. for 30 minutes to 5 hours.

Method (3): The carboxylic acid derivatives of formula (I) wherein $R^2$ is hydrogen can be prepared by hydrolyzing a compound of the formula (II) or (V) in a conventional manner.

The carboxylic acid derivatives can be converted into, for example, sodium salt, potassium salt, carcium salt and aluminium salt according to a conventional manner.

The compounds of formula (I) and salts thereof have potent immunomodulatory activities and very low toxicities as shown, for example, by the following pharmacological experiments:

TEST METHODS (I) Activity for potentiating production of rosette forming cells As test animals, 6-week old female C57L/6-strain mice were used by dividing them into groups of 6 members. The sensitization was made by the intraperitoneal administration of the antigen; $5 \times 10^8$ sheep red blood cells. The test compounds were orally administered to the animals at the day of sensitization and the next day. Seven days after sensitization, the number of rosette forming cells in the spleen and thymus was measured in a usual manner. The results are shown in Table 1.

It can be understood that the compounds of the present invention have immunopotentiating activities since the increase of the number of rosette forming cells can be observed in the groups treated with the compounds of the present invention as apparently shown in Table 1.

(II) Activity for supressing production of rosette forming cells

As test animals, 6-week old female BALB/C-strain mice were used by dividing them into groups of 6 members. The sensitization was made by the intrapetoneal administration of the antigen; $5 \times 10^8$ sheep red blood cells. The test compounds were orally administered to the animals at the day of sensitization and the next day. Four days after sensitization, the number of rosette forming cells in the spleen and thymus was measured in a usual manner. The results are shown in Table 2.

It can be understood that the compounds of the present invention have immunosupressing activities since the decrease of the number of rosette forming cells can be observed in the groups treated with the compounds of the present invention as apparently shown in Table 2.

TEST COMPOUNDS

Compound A: Ethyl 4-[2-(4-methoxyphenyl)-3-indolizinyl]-2,4-dioxobutyrate

Compound B: Ethyl 4-[2-(4-methylthiophenyl)-3-indolizinyl]-2,4-dioxobutyrate

Compound C: Ethyl 4-[2-(4-methylthiophenyl)imidazo [1,2-a]pyridin-3-yl]-2,4-dioxobutyrate Compound D: Ethyl 4-[6-(4-methoxyphenyl)imidazo [2,1-b]thiazol-5-yl]-2,4-dioxobutyrate

RESULTS

TABLE 1

| Test Compound | Dose (mg/kg) | Number of rosette forming cells ($\times 10^4$) | |
|---|---|---|---|
| | | Spleen | Thymus |
| A | 10 | 129 ± 38 | 16.14 ± 4.87** |
| Control | 0 | 113 ± 24 | 3.40 ± 0.29 |
| B | 10 | 145 ± 20** | 7.62 ± 2.14* |
| Control | 0 | 28 ± 13 | 2.37 ± 0.96 |
| C | 10 | 183 ± 47* | 9.56 ± 1.35** |
| Control | 0 | 97 ± 16 | 3.04 ± 1.12 |
| D | 10 | 84 ± 9 | 6.67 ± 0.98* |
| Control | 0 | 49 ± 10 | 2.52 ± 0.55 |

The asterisks * and ** indicate that the values marked with them are significant against the control groups;
*$p < 0.05$;
**$p < 0.01$, respectively.

TABLE 2

| Test Compound | Dose (mg/kg) | Number of rosette forming cells ($\times 10^4$) | |
|---|---|---|---|
| | | Spleen | Thymus |
| A | 30 | 59 ± 8 | 2.00 ± 0.47 |
| Control | 0 | 71 ± 17 | 3.41 ± 0.96 |
| B | 100 | 76 ± 10** | 1.56 ± 0.54* |
| B | 10 | 122 ± 26 | 3.11 ± 0.80 |
| Control | 0 | 150 ± 23 | 5.70 ± 1.10 |
| C | 10 | 183 ± 20* | 3.93 ± 1.05** |
| Control | 0 | 244 ± 26 | 7.70 ± 1.08 |
| D | 30 | 58 ± 8 | 1.21 ± 0.21** |
| Control | 0 | 71 ± 17 | 3.41 ± 0.96 |

The asterisks * and ** indicate that the values marked with them are significant against the control groups;
*$p < 0.05$;
**$p < 0.01$, respecitively.

No toxicity observed when each 1000 mg/kg of test compounds A to D was orally administered to 8-week old male dd-strain mice.

From various viewpoints including the above-mentioned pharmacological experiments, the compounds of formula (I) and salts thereof have potent immunomodulatory activities, so that it can be said that those compounds of the present invention are useful as drugs for treating immune diseases such as rheumatoid arthritis, rheumatism, allergy, cancer, autoimmune diseases or bacterial infectious diseases.

The compounds of formula (I) and salts thereof can be administered safely as immunomodulators in the form of a pharmaceutical preparation with a suitable and conventional carrier or adjuvant without harmful side effects to the patients.

The pharmaceutical preparation for oral administration can take the form of tablets, sugar-coated tablets, granules, powder, capsules, etc., and sometimes can take the form of injectable solution for subcutaneous or intramuscular administration. The choice of carrier is determined by the preferred form of administration, the solubility of the compound employed and standard pharmaceutical practise.

The daily dose of the compounds of formula (I) for human adults usually ranges from 100 to 1000 mg for oral administration, in single or multiple dose, but it may vary depending upon body weight, age or severity of the condition to be treated.

The present invention will be further explained by way of the following illustrative examples in more detail, but they are not to be construed as limiting the present invention.

EXAMPLE 1

To a solution of 25.7 g of methyl 2-phenyl-3-indolizinyl ketone in 360 ml of benzene were added 8.3 g of 50% sodium hydride and 28.2 g of diethyl oxalate, and the mixture was heated at 60° C. for 30 minutes. After cooling, the benzene was distilled off. To the residue was added 200 ml of water and the aqueous solution was acidified with acetic acid. Crystals precipitated were filtered off and washed with water, and then recerystallized from ethanol to give 30 g of ethyl 4-(2-phenyl-3-indolizinyl)-2,4-dioxobutyrate, melting at 100°–102° C.

The following compounds can be prepared in a similar manner mentioned in the Example 1:

Ethyl 4-(2-ethyl-3-indolizinyl)-2,4-dioxobutyrate, melting at 102°–104° C.

Ethyl 4-[2-(4-methoxyphenyl)-3-indolizinyl]-2,4-dioxobutyrate, melting at 116°–118° C.

Ethyl 4-[2-(4-bromophenyl)-3-indolizinyl]-2,4-dioxobutyrate, melting at 155°–157° C.

Ethyl 4-(7-methyl-2-phenyl-3-indolizinyl)-2,4-dioxobutyrate, melting at 150°–152° C.

Ethyl 4-[2-(3,4-dichlorophenyl)-3-indolizinyl]-2,4-dioxobutyrate, melting at 136°–138° C.

Ethyl 4-[2-(3,4-dimethoxyphenyl)-3-indolizinyl]-2,4-dioxobutyrate, melting at 142°–145° C.

Ethyl 4-[2-(4-(methylthiophenyl)-3-indolizinyl]-2,4-dioxobutyrate, melting at 143°–145° C.

Ethyl 4-[2-(4-methylsulfinylphenyl)-3-indolizinyl]-2,4-dioxobutyrate, melting at 170°–173° C.

Ethyl 4-[2-(4-methoxyphenyl)-3-indolizinyl]-2,4-dioxobutyrate, melting at 131°–133° C.

Ethyl 4-[2-(4-methoxyphenyl)-1-methyl-3-indolizinyl]-2,4-dioxobutyrate, melting at 139°–141° C.

Ethyl 4-(2-phenylimidazo[1,2-a]pyridin-3-yl)-2,4-dioxobutyrate, melting at 139°–140° C.

Ethyl 4-[2-(4-methylthiophenyl)imidazo[1,2-a]pyridin-3-yl]-2,4-dioxobutyrate, melting at 157°–159° C.

Ethyl 4-[2-(4-methoxyphenyl)imidazo[1,2-a]pyridin-3-yl]-2,4-dioxobutyrate, melting at 142°–144° C.

Ethyl 4-[2-(4-methoxyphenyl)imidazo[2,1-b]thiazol-5-yl]-2,4-dioxobutyrate, melting at 141°–143° C.

Ethyl 4-[6-(4-methoxyphenyl)-3-methylimidazo[2,1-b]thiazol-5-yl]-2,4-dioxobutyrate, melting at 139°–140° C.

Ethyl 4-[2-(4-(2-(N,N-dimethylamino)ethoxy)phenyl)-3-indolizinyl]-2,4-dioxobutyrate, melting at 100°–103° C.
Ethyl 4-[2-(4-(2-(N,N-diethylamino)ethoxy)phenyl)-3-indolizinyl]-2,4-dioxobutyrate
Ethyl 4-[2-(4-(3-(N,N-dimethylamino)propoxy)phenyl)-3-indolizinyl]-2,4-dioxobutyrate
Ethyl 4-[2-(4-cyanophenyl)-3-indolizinyl]-2,4-dioxobutyrate
Ethyl 4-[2-(4-methylphenyl)-3-indolizinyl]-2,4-dioxobutyrate
Ethyl 4-[2-(4-nitrophenyl)-3-indolizinyl]-2,4-dioxobutyrate
Ethyl 4-[2-(4-aminophenyl)-3-indolizinyl]-2,4-dioxobutyrate
Ethyl 4-[2-(2-thienyl)-3-indolizinyl]-2,4-dioxobutyrate
Ethyl 4-[2-(2-furyl)-3-indolizinyl]-2,4-dioxobutyrate
Ethyl 5-(2-phenyl-3-indolizinyl)-2,4-dioxovalerate
4-[2-(4-Methoxyphenyl)-3-indolizinyl]-2,4-dioxobutyric acid
4-[2-(4-Methylthiophenyl)-3-indolizonyl]-2,4-dioxobutyric acid
4-[2-(3,4-Dichlorophenyl)-3-indolizinyl]-2,4-dioxobutyric acid
4-[2-(3,4-Dimethoxyphenyl)-3-indolizinyl]-2,4-dioxobutyric acid
4-[2-(4-Bromophenyl)-3-indolizinyl]-2,4-dioxobutyric acid
4-[2-(4-Methylthiophenyl)imidazo[1,2-a]pyridin-3-yl]-2,4-dioxobutyric acid
4-[6-(4-Methoxyphenyl)imidazo[2,1-b]thiazol-5-yl]-2,4-dioxobutyric acid
4-[6-(4-Methylthiophenyl)imidazo[2,1-b]thiazol-5-yl]-2,4dioxobutyric acid
4-(2-Phenyl-3-indolizinyl)-2,4-dioxobutyric acid

EXAMPLE 2

To a suspension of 10.2 g of 2-phenylindolizine in 150 ml of benzene were added 6 ml of pyridine and 9.6 g of β-methoxycarbonylpropionyl chloride and the mixture was refluxed overnight. After cooling, 50 ml of water was added and the whole mixture was extracted with benzene. After the extract was decolorized and concentrated, to the residue was added 30 ml of isopropyl ether and the mixture was cooled to precipitate methyl 4-(2-phenyl-3-indolizinyl)-4-oxobutyrate. The precipitate was filtered off and then this ester compound was hydrolyzed in a conventional manner to give 8.3 g of 4-(2-phenyl-3-indolizinyl)-4-oxobutyric acid, melting at 131°–133° C.

The following compounds can be prepared in a similar manner mentioned in the Example 2:

4-(2-Ethyl-3-indolizinyl)-4-oxobutyric acid, melting at 119°–121° C.
Methyl 4-(2-ethyl-3-indolizinyl)-4-oxobutyrate
4-(2-Methyl-3-indolizinyl)-4-oxobutyric acid
4-[2-(3,4-Dimethoxyphenyl)-3-indolizinyl]-4-oxobutyric acid
4-[2-(3,4-Dichlorophenyl)-3-indolizinyl]-4-oxobutyric acid
4-[2-(4-Bromophenyl)-3-indolizinyl]-4-oxobutyric acid
4-[2-(4-Methylphenyl)-3-indolizinyl]-4-oxobutyric acid
4-[2-(4-Chlorophenyl)-3-indolizinyl]-4-oxobutyric acid
4-[2-(4-Methylthiophenyl)-3-indolizinyl]-4-oxobutyric acid
4-[2-(4-Methoxyphenyl)indolizinyl]-4-oxobutyric acid
4-[2-(4-Cyanophenyl)-3-indolizinyl]-4-oxobutyric acid
4-[2-(4-Nitrophenyl)-3-indolizinyl]-4-oxobutyric acid
4-[2-(4-Aminophenyl)-3-indolizinyl]-4-oxobutyric acid
Ethyl 3-(2-phenyl-3-indolizinyl)-3-oxopropionate, melting at 86°–88° C.
Ethyl 4-[2-(4-methoxyphenyl)-3-indolizinyl]-4-oxobutyrate
Ethyl 3-[2-(4-methoxyphenyl)-3-indolizinyl]-3-oxopropionate
Ethyl 3-[2-(4-bromophenyl)-7-methyl-3-indolizinyl]-3-oxopropionate
Ethyl 4-[2-(2-thienyl)-3-indolizinyl]-4-oxobutyrate
Ethyl 4-[2-(2-furyl)-3-indolizinyl]-4-oxobutyrate
Ethyl 3-[2-(2-thienyl)-3-indolizinyl]-3-oxopropionate Formulation Example 60 mg tablets are prepared from the following composition:

| | |
|---|---|
| Ethyl 4-[2-(4-methylthiophenyl)-3-indolizinyl]-2,4-dioxobutyrate | 60.0 mg |
| Lactose | 52.8 mg |
| Corn Starch | 35.0 mg |
| Microcrystalline Cellulose | 20.0 mg |
| Methyl Cellulose | 2.0 mg |
| Talc | 4.5 mg |
| Magnesium Stearate | 0.7 mg |
| | 175.0 mg |

Although the present invention has been adequately discussed in the foregoing specification and examples included therein, one readily recognizes that various changes and modifications may be made without departing from the spirit and the scope thereof.

What is claimed is:

1. A compound of the formula:

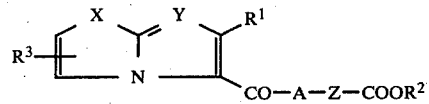

wherein $R^1$ is hydrogen, lower alkyl, phenyl which may be substituted by at least one substituent selected from halogen, lower alkyl, lower alkoxy, mono- or di-lower alkyl amino-substituted lower alkoxy, lower alkylthio, lower alkylsulfinyl, amino, nitro and cyano at any position(s) on the nucleus, thienyl or furyl, each of $R^2$ and $R^3$ is hydrogen or lower alkyl, A is lower alkylene, X is sulfur or vinylene, Y is nitrogen or methine which may be substituted by lower alkyl, and Z is carbonyl or direct bond.

2. The compound of claim 1:
Ethyl 4-[2-(4-methoxyphenyl)-3-indolizinyl]-2,4-dioxobutyrate.

3. The compound of claim 1:
Ethyl 4-[2-(4-methylthiophenyl)-3-indolizinyl]-2,4-dioxobutyrate.

4. The compound of claim 1:
Ethyl 4-[2-(4-methylthiophenyl)imidazo[1,2-a]pyridin-3-yl]-2,4-dioxobutyrate.

5. The compound of claim 1:

Ethyl 4-[6-(4-methoxyphenyl)imidazo[2,1-b]thiazol-5-yl]-2,4-dioxobutyrate.

6. The compound of claim 1:

Ethyl 4-[6-(4-methylthiophenyl)imidazo[2,1-b]thiazol-5-yl]-2,4-dioxobutyrate.

7. The compound of claim 1:

Ethyl 4-[2-(3,4-dichlorophenyl)-3-indolizinyl]-2,4-dioxobutyrate.

8. The compound of claim 1:

Ethyl 4-[2-(3,4-dimethoxyphenyl)-3-indolizinyl]-2,4-dioxobutyrate.

9. The compound of claim 1:

Ethyl 4-[2-(4-bromophenyl)-3-indolizinyl]-2,4-dioxobutyrate.

10. A pharmaceutical composition having immunomodulatory activity comprising an immunomodulatorily effective amount of a compound of claim 1 in combination with a pharmaceutically acceptable carrier.

* * * * *